(12) United States Patent
Sorgenfrei et al.

(10) Patent No.: US 11,735,681 B2
(45) Date of Patent: *Aug. 22, 2023

(54) PHOTODETECTOR SYSTEMS WITH LOW-POWER TIME-TO-DIGITAL CONVERTER ARCHITECTURES TO DETERMINE AN ARRIVAL TIME OF PHOTON AT A PHOTODETECTOR BASED ON EVENT DETECTION TIME WINDOW

(71) Applicant: HI LLC, Los Angeles, CA (US)

(72) Inventors: Sebastian Sorgenfrei, Playa Vista, CA (US); Jacob Dahle, Arlington, MA (US); Ryan Field, Culver City, CA (US); Bruno Do Valle, Brighton, MA (US); Rong Jin, Acton, MA (US)

(73) Assignee: HI LLC, Los Angeles, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/725,703

(22) Filed: Apr. 21, 2022

(65) Prior Publication Data

US 2022/0246783 A1 Aug. 4, 2022

Related U.S. Application Data

(63) Continuation of application No. 17/095,287, filed on Nov. 11, 2020, now Pat. No. 11,398,578, which is a
(Continued)

(51) Int. Cl.
*A61B 5/00* (2006.01)
*H01L 31/107* (2006.01)
*H01L 31/02* (2006.01)

(52) U.S. Cl.
CPC ...... *H01L 31/107* (2013.01); *H01L 31/02027* (2013.01)

(58) Field of Classification Search
CPC . G01S 7/486; G01S 17/86; A61B 5/00; A61B 5/68; G04F 8/00; G04F 10/00; H01L 31/02; H01L 31/107
(Continued)

(56) References Cited

U.S. PATENT DOCUMENTS 5,853,370 A 12/1998 Chance et al.
6,240,309 B1 5/2001 Yamashita et al.
(Continued)

FOREIGN PATENT DOCUMENTS

WO 2018033751 2/2018

OTHER PUBLICATIONS

Alayed, et al., "Characterization of a Time-Resolved Diffuse Optical Spectroscopy Prototype Using Low-Cost, Compact Single Photon Avalanche Detectors for Tissue Optics Applications", Sensors 2018, 18, 3680; doi:10.3390/s18113680, Oct. 29, 2018.
(Continued)

*Primary Examiner* — Que Tan Le
(74) *Attorney, Agent, or Firm* — ALG Intellectual Property, LLC

(57) ABSTRACT

An illustrative system may include a component configured to be worn on a body of a user, the component comprising a time-to-digital converter (TDC) configured to: receive, during a predetermined event detection time window that commences in response to an application of a light pulse to a target within the body, a signal triggered by an event in which a photodetector detects a photon of the light pulse after the light pulse reflects from the target; and measure, based on the receiving the signal, a time interval between when the event occurred and an end of the predetermined event detection time window. The system may further include a processor configured to determine, based on the
(Continued)

time interval and the predetermined event detection time window, an arrival time of the photon at the photodetector.

20 Claims, 13 Drawing Sheets

Related U.S. Application Data continuation of application No. 16/880,686, filed on May 21, 2020, now Pat. No. 10,868,207.

(60) Provisional application No. 62/906,620, filed on Sep. 26, 2019, provisional application No. 62/858,029, filed on Jun. 6, 2019.

(58) Field of Classification Search
USPC ...................................... 250/214 R, 239, 221
See application file for complete search history.

(56) References Cited

U.S. PATENT DOCUMENTS

| | | |
|---|---|---|
| 6,384,663 B2 | 5/2002 | Cova et al. |
| 6,640,133 B2 | 10/2003 | Yamashita |
| 6,683,294 B1 | 1/2004 | Herbert et al. |
| 7,356,365 B2 | 4/2008 | Schurman |
| 7,547,872 B2 | 6/2009 | Niclass et al. |
| 7,774,047 B2 | 8/2010 | Yamashita et al. |
| 8,026,471 B2 | 9/2011 | Itzler |
| 8,078,250 B2 | 12/2011 | Chen et al. |
| 8,082,015 B2 | 12/2011 | Yodh et al. |
| 8,633,431 B2 | 1/2014 | Kim |
| 8,817,257 B2 | 8/2014 | Herve |
| 9,058,081 B2 | 6/2015 | Baxter |
| 9,076,707 B2 | 7/2015 | Harmon |
| 9,131,861 B2 | 9/2015 | Ince et al. |
| 9,316,735 B2 | 4/2016 | Baxter |
| 9,401,448 B2 | 7/2016 | Bienfang et al. |
| 9,419,635 B2 | 8/2016 | Kumar et al. |
| 9,442,201 B2 | 9/2016 | Schmand et al. |
| 9,529,079 B1 | 12/2016 | Droz |
| 9,574,936 B2 | 2/2017 | Heinonen |
| 9,946,344 B2 | 4/2018 | Ayaz et al. |
| D817,553 S | 5/2018 | Aaskov et al. |
| D825,112 S | 8/2018 | Saez |
| 10,158,038 B1 | 12/2018 | Do Valle et al. |
| 10,340,408 B1 | 7/2019 | Katnani |
| 10,424,683 B1 | 9/2019 | Do Valle |
| 10,515,993 B2 | 12/2019 | Field et al. |
| 10,558,171 B2 | 2/2020 | Kondo |
| 10,697,829 B2 | 6/2020 | Delic |
| 10,772,561 B2 | 9/2020 | Donaldson |
| 10,809,796 B2 | 10/2020 | Armstrong-Muntner |
| 10,912,504 B2 | 2/2021 | Nakaji |
| 11,006,876 B2 | 5/2021 | Johnson |
| 11,006,878 B2 | 5/2021 | Johnson |
| 11,096,620 B1* | 8/2021 | Seidman ............ G01N 33/4833 |
| 11,172,869 B2 | 11/2021 | Johnson |
| 2007/0083097 A1 | 4/2007 | Fujiwara |
| 2009/0012402 A1 | 1/2009 | Mintz |
| 2011/0208675 A1 | 8/2011 | Shoureshi et al. |
| 2013/0342835 A1 | 12/2013 | Blacksberg |
| 2014/0191115 A1 | 7/2014 | Webster et al. |
| 2014/0217264 A1 | 8/2014 | Shepard |
| 2014/0275891 A1 | 9/2014 | Muehlemann et al. |
| 2015/0038811 A1 | 2/2015 | Asaka |
| 2015/0041625 A1 | 2/2015 | Dutton |
| 2015/0054111 A1 | 2/2015 | Niclass et al. |
| 2015/0077279 A1 | 3/2015 | Song |
| 2015/0150505 A1 | 6/2015 | Kaskoun et al. |
| 2015/0327777 A1 | 11/2015 | Kostic et al. |
| 2015/0364635 A1 | 12/2015 | Bodlovic et al. |
| 2017/0030769 A1 | 2/2017 | Clemens et al. |
| 2017/0052065 A1 | 2/2017 | Sharma et al. |
| 2017/0176596 A1 | 6/2017 | Shpunt et al. |
| 2017/0179173 A1 | 6/2017 | Mandai et al. |
| 2017/0202518 A1 | 7/2017 | Furman et al. |
| 2017/0281086 A1 | 10/2017 | Donaldson |
| 2017/0363467 A1 | 12/2017 | Clemens et al. |
| 2017/0367650 A1 | 12/2017 | Wallois |
| 2018/0014741 A1 | 1/2018 | Chou |
| 2018/0027196 A1 | 1/2018 | Yang et al. |
| 2018/0039053 A1 | 2/2018 | Kremer et al. |
| 2018/0070830 A1 | 3/2018 | Sutin et al. |
| 2018/0070831 A1 | 3/2018 | Sutin et al. |
| 2018/0089848 A1 | 3/2018 | Yang et al. |
| 2019/0113385 A1 | 4/2019 | Fukuchi |
| 2019/0175068 A1 | 6/2019 | Everdell |
| 2019/0355861 A1 | 11/2019 | Katnani |
| 2019/0363210 A1 | 11/2019 | Do Valle |
| 2019/0388018 A1 | 12/2019 | Horstmeyer |
| 2020/0060542 A1 | 2/2020 | Alford |
| 2020/0116838 A1 | 4/2020 | Erdogan |
| 2020/0196932 A1 | 6/2020 | Johnson |
| 2020/0253479 A1 | 8/2020 | Nurmikko |
| 2020/0315510 A1 | 10/2020 | Johnson |
| 2020/0337624 A1 | 10/2020 | Johnson |
| 2020/0390358 A1 | 12/2020 | Johnson |

OTHER PUBLICATIONS

Ban, et al., "Kernel Flow: a high channel count scalable TD-fNIRS system", https://www.spiedigitallibrary.org/conference-proceedings-of-spie Proc. of SPIE vol. 11663, 116630B doi: 10.1117/12.2582888, Mar. 5, 2021.

Ban, et al., "Kernel Flow: a high channel count scalable time-domain functional near-infrared spectroscopy system", https://www.spiedigitallibraryorg/journals/Journal-of-Biomedical-Optics on Jan. 18, 2022.

Contini, et al., "Photon migration through a turbid slab described by a model based on diffusion approximation. I. Theory", Appl. Opt. 36(19), 4587 (1997).

Di Sieno, et al., "Probe-hosted large area silicon photomultiplier and high-throughput timing electronics for enhanced performance time-domain functional near-infrared spectroscopy", Biomed Opt. Express 11 (11), 6389 (2020).

Fishburn, et al., "Temporal Derivative Distribution Repair (TDDR): A motion correction method for fNIRS", Neuroimage. Jan. 1, 2019; 184: 171-179. doi:10.1016/j.neuroimage.2018.09.025.

Huppert, et al., "HomER: a review of time-series analysis methods for near-infrared spectroscopy of the brain", Appl. Opt. 48(10), D280 (2009).

Kienle, et al., "Improved solutions of the steady-state and the time-resolved diffusion equations for reflectance from a semi-infinite turbid medium", J. Opt. Soc. Am. A 14(1), 246 (1997).

Konugolu, et al., "Broadband (600-1350 nm) Time-Resolved Diffuse Optical Spectrometer for Clinical Use", IEEE Journal of Selected Topics in Quantum Electronics, vol. 22, No. 3, May/Jun. 2016.

Lacerenza, et al., "Wearable and wireless time-domain near-infrared spectroscopy system for brain and muscle hemodynamic monitoring", Biomed. Opt. Express 11(10), 5934 (2020).

Lange, et al., "Clinical Brain Monitoring with Time Domain NIRS: A Review and Future Perspectives", Applied Sciences 9(8), 1612(2019).

Lange, et al., "Maestros: A Multiwavelength Time-Domain NIRS System to Monitor Changes in Oxygenation and Oxidation State of Cytochrome-C-Oxidase", IEEE J. Select. Topics Quantum Electron. 25(1), 1-12 (2019).

Martelli, et al., "Optimal estimation reconstruction of the optical properties of a two-layered tissue phantom from time-resolved single-distance measurements", Journal of Biomedical Optics 20(11), 115001 (Nov. 2015).

Mora, et al., "Fast silicon photomultiplier improves signal harvesting and reduces complexity in time-domain diffuse optics", Opt. Express 23(11), 13937 (2015).

Pifferi, et al., "Performance assessment of photon migration instruments: the MEDPHOT protocol", Applied Optics, 44(11), 2104-2114, 2005.

(56) References Cited

OTHER PUBLICATIONS

Prahl, et al., "Optical Absorption of Hemoglobin", http://omlc.ogi.edu/spectra/hemoglobin/index.html, 1999.

Re, et al., "Multi-channel medical device for time domain functional near infrared spectroscopy based on wavelength space multiplexing", Biomed Opt. Express 4(10), 2231 (2013).

Renna, et al., "Eight-Wavelength, Dual Detection Channel Instrument for Near-Infrared Time-Resolved Diffuse Optical Spectroscopy", IEEE J. Select. Topics Quantum Electron. 25(1), 1-11 (2019).

Torricelli, et al., "Time domain functional NIRS imaging for human brain mapping", NeuroImage 85, 28-50 (2014).

Wabnitz, et al., "Depth-selective data analysis for time-domain fNIRS: moments vs. time windows", Biomed. Opt. Express 11(8), 4224 (2020).

Wabnitz, et al., "Performance assessment of time-domain optical brain imagers, part 1: basic instrumental performance protocol", Journal of Biomedical Optics 19(8), 086010 (Aug. 2014).

Wabnitz, et al., "Performance assessment of time-domain optical brain imagers, part 2: nEUROPt protocol", Journal of Biomedical Optics 19(8), 086012 (Aug. 2014).

Wojtkiewicz, et al., "Self-calibrating time-resolved near infrared spectroscopy", Biomed. Opt. Express 10(5), 2657 (2019).

Zucchelli, et al., "Method for the discrimination of superficial and deep absorption variations by time domain fNIRS", 2013 OSA Dec. 1, 2013 | vol. 4, No. 12 | DOI:10.1364/BOE.4.002893 | Biomedical Optics Express 2893, 2013.

\* cited by examiner

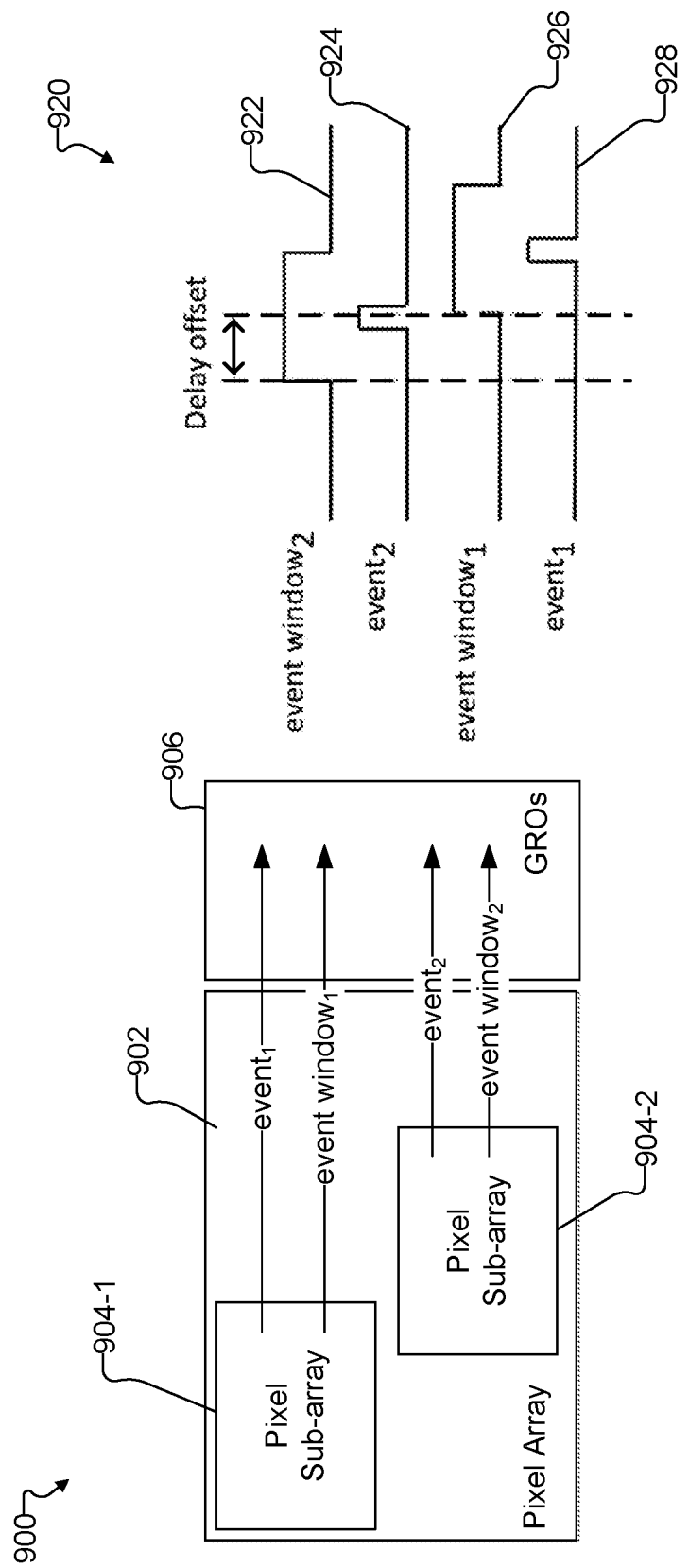

PHOTODETECTOR SYSTEMS WITH LOW-POWER TIME-TO-DIGITAL CONVERTER ARCHITECTURES TO DETERMINE AN ARRIVAL TIME OF PHOTON AT A PHOTODETECTOR BASED ON EVENT DETECTION TIME WINDOW

RELATED APPLICATIONS

This application is a continuation application of U.S. patent application Ser. No. 17/095,287, filed Nov. 11, 2020, which is a continuation application of U.S. patent application Ser. No. 16/880,686, filed May 21, 2020, now U.S. Pat. No. 10,868,207, which application claims priority under 35 U.S.C. § 119(e) to U.S. Provisional Patent Application No. 62/906,620, filed Sep. 26, 2019, and to U.S. Provisional Patent Application No. 62/858,029 filed Jun. 6, 2019. These applications are incorporated herein by reference in their respective entireties.

BACKGROUND INFORMATION

Detecting neural activity in the brain is useful for medical diagnostics, imaging, neuroengineering, brain-computer interfacing, and a variety of other diagnostic and consumer-related applications. For example, it may be desirable to detect neural activity in the brain of a patient to determine if a particular region of the brain has been impacted by reduced blood irrigation, a hemorrhage, or any other type of damage. As another example, it may be desirable to detect neural activity in the brain of a user and computationally decode the detected neural activity into commands that can be used to control various types of consumer electronics (e.g., by controlling a cursor on a computer screen, changing channels on a television, turning lights on, etc.).

A photodetector capable of detecting a single photon (i.e., a single particle of optical energy) is an example of a non-invasive detector that can be used to detect neural activity within the brain. For example, an array of these sensitive photodetectors can record photons that reflect off of tissue within the brain in response to application of one or more light pulses. Based on the time it takes for the photons to be detected by the photodetectors, neural activity and other attributes of the brain can be determined or inferred.

Time-to-digital converters (TDCs) are used in conjunction with photodetectors to convert a timing event or timing interval (e.g., an amount of time that it takes for a photon of a light pulse to be detected by a photodetector after the pulse of light is applied to a target) into a digital representation. Conventionally, phase-locked loops or delay-locked loops are used to provide a phase and delay information to capture a digitized value with a specific timing resolution. However, synchronizing TDCs and/or components of TDCs may consume a relatively high amount of power.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

FIG. 9A illustrates an exemplary photodetector system with a low-power TDC architecture according to principles described herein.

FIG. 9B illustrates an exemplary timing diagram for an exemplary photodetector system with a low-power TDC architecture according to principles described herein.

DETAILED DESCRIPTION

Photodetector systems with low-power TDC architectures are described herein. The systems described herein include a photodetector, a TDC coupled to the photodetector, and a control circuit coupled to the TDC. The TDC is configured to receive, during a predetermined event detection time window that commences in response to an application of a light pulse to a target, a signal triggered by an event in which the photodetector detects a photon of the light pulse after the light pulse reflects from the target, the signal configured to enable a gated ring oscillator (GRO) of the TDC. The TDC is further configured to measure, using the GRO, a time interval between when the event occurred and an end of the predetermined event detection time window. The control circuit is configured to determine, based on the time interval and the predetermined event detection time window, an arrival time of the photon at the photodetector.

As the TDC architectures described herein enable a GRO and/or other components of the TDC in response to the event in which the photon is detected, the TDC architectures may conserve power until such events occur. For a photodetector system including a plurality of photodetectors for which many of the photodetectors detect photons relatively infrequently, such an event-driven TDC architecture may result in a substantial reduction of power consumption compared to conventional photodetector systems. Further, components conventionally used to synchronize a plurality of TDCs may be unnecessary as the TDCs are disabled and enabled, resulting in further reduction of power usage as well as reduction in system area. These and other benefits and/or advantages that may be provided by the systems and methods described herein will be made apparent by the following detailed description.

Figure 1:
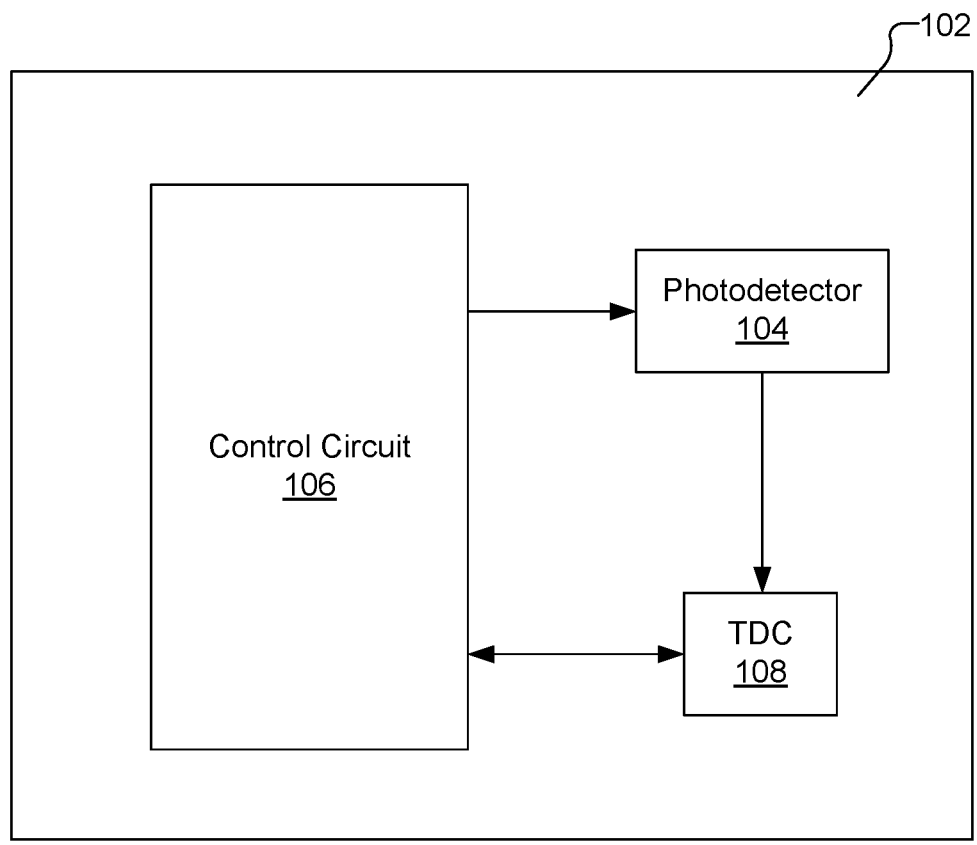
FIG. 1 illustrates an exemplary photodetector with a low-power TDC architecture according to principles described herein.

FIG. 1 illustrates an exemplary photodetector system 102 with a low-power TDC architecture. As shown, photodetector system 102 includes a photodetector 104, a control circuit 106, and a TDC 108. In some examples, photodetector system 102 may include more, fewer, and/or different components. For example, photodetector system 102 may include a plurality of photodetectors, a plurality of TDCs corresponding to the photodetectors, and one or more control circuits for the photodetectors and TDCs.

Photodetector 104 may be implemented by any suitable circuit configured to detect individual photons of light incident upon photodetector 104. For example, photodetector 104 may be implemented by a single photon avalanche diode (SPAD) circuit including a SPAD and a fast gating circuit configured to operate together to detect a photon incident upon the SPAD. Photodetector 104 may generate an output when the SPAD detects a photon.

TDC 108 is configured to measure a time difference between an occurrence of a light pulse and an occurrence of an output signal generated by photodetector 104 indicating that SPAD circuit 104 has detected a photon from the light pulse after the light pulse reflected from a target. Example implementations of TDC 108 are described herein.

Control circuit 106 may be implemented by an application specific integrated circuit (ASIC) or any other suitable circuit configured to control an operation of various components within photodetector 104 (e.g., a SPAD circuit) and TDC 108.

For example, control circuit 106 may output control logic that controls an operation of one or more switches within the SPAD circuit to selectively put the SPAD included in photodetector 104 in either an armed or a disarmed state (e.g., by selectively charging a capacitor within the SPAD circuit). In some examples, control circuit 106 may control a gate delay, which specifies a predetermined amount of time control circuit 106 is to wait after an occurrence of a light pulse (e.g., a laser pulse) to put the SPAD in the armed state. To this end, control circuit 106 may receive light pulse timing information, which indicates a time at which a light pulse occurs (e.g., a time at which the light pulse is applied to a target, such as tissue within the brain). Control circuit 106 may also control a programmable gate width, which specifies how long the SPAD is kept in the armed state before being disarmed. For example, control circuit 106 may keep the SPAD in the armed state for a predetermined event detection time window.

Control circuit 106 may also be configured to control an operation of TDC 108. For example, as described herein, control circuit 106 may generate one or more signals used to enable and/or disable a GRO and/or other components within TDC 108.

Control circuit 106 may be further configured to perform one or more signal processing operations on data output by TDC 108. For example, signal processing circuit 110 may generate histogram data based on the data output by TDC 108 and in accordance with histogram parameters (e.g., time bins, number of light pulses, type of histogram, etc.) accessed by control circuit 106. To illustrate, control circuit 106 may generate, store, transmit, compress, analyze, decode, and/or otherwise process histograms based on the data output by TDC 108. In some examples, signal processing operations may be performed by a separate additional component.

Figure 2:
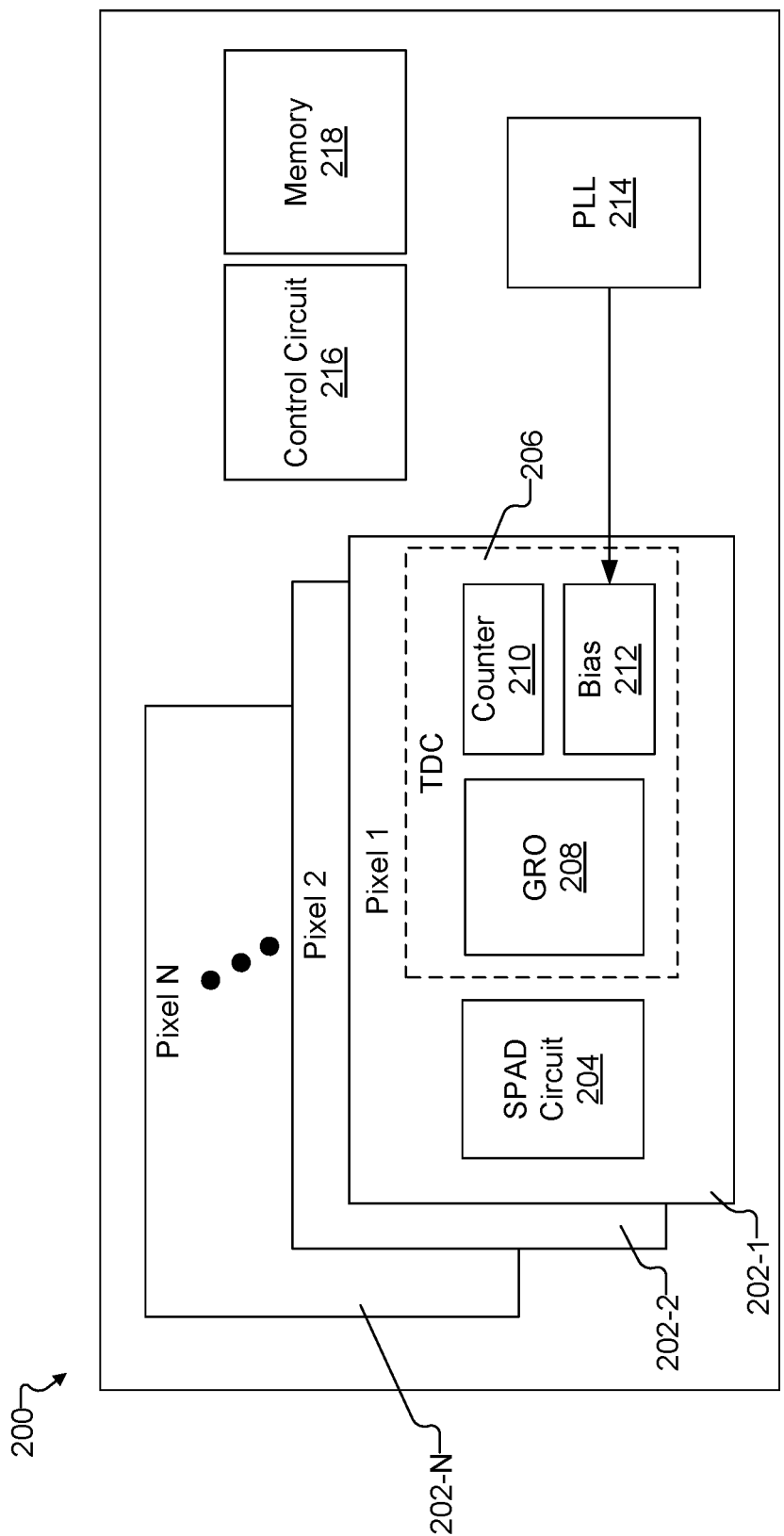
FIG. 2 illustrates an exemplary photodetector system with low-power TDC architectures according to principles described herein.

FIG. 2 illustrates an exemplary photodetector system 200 with low-power TDC architectures. Photodetector system 200 includes photodetector pixels 202 (e.g., photodetector pixel 1 202-1 through photodetector pixel N 202-N). Each of photodetector pixels 202, such as photodetector pixel 202-1, includes a SPAD circuit 204 and a TDC 206. TDC 206 includes a GRO 208, a counter 210, and a bias generator 212. Bias generator 212 may receive a signal from a phase-locked loop (PLL) 214. Photodetector system 200 further includes a control circuit 216 (e.g., an implementation of control circuit 106) corresponding to one or more of photodetector pixels 202 and a memory 218.

Figure 3:
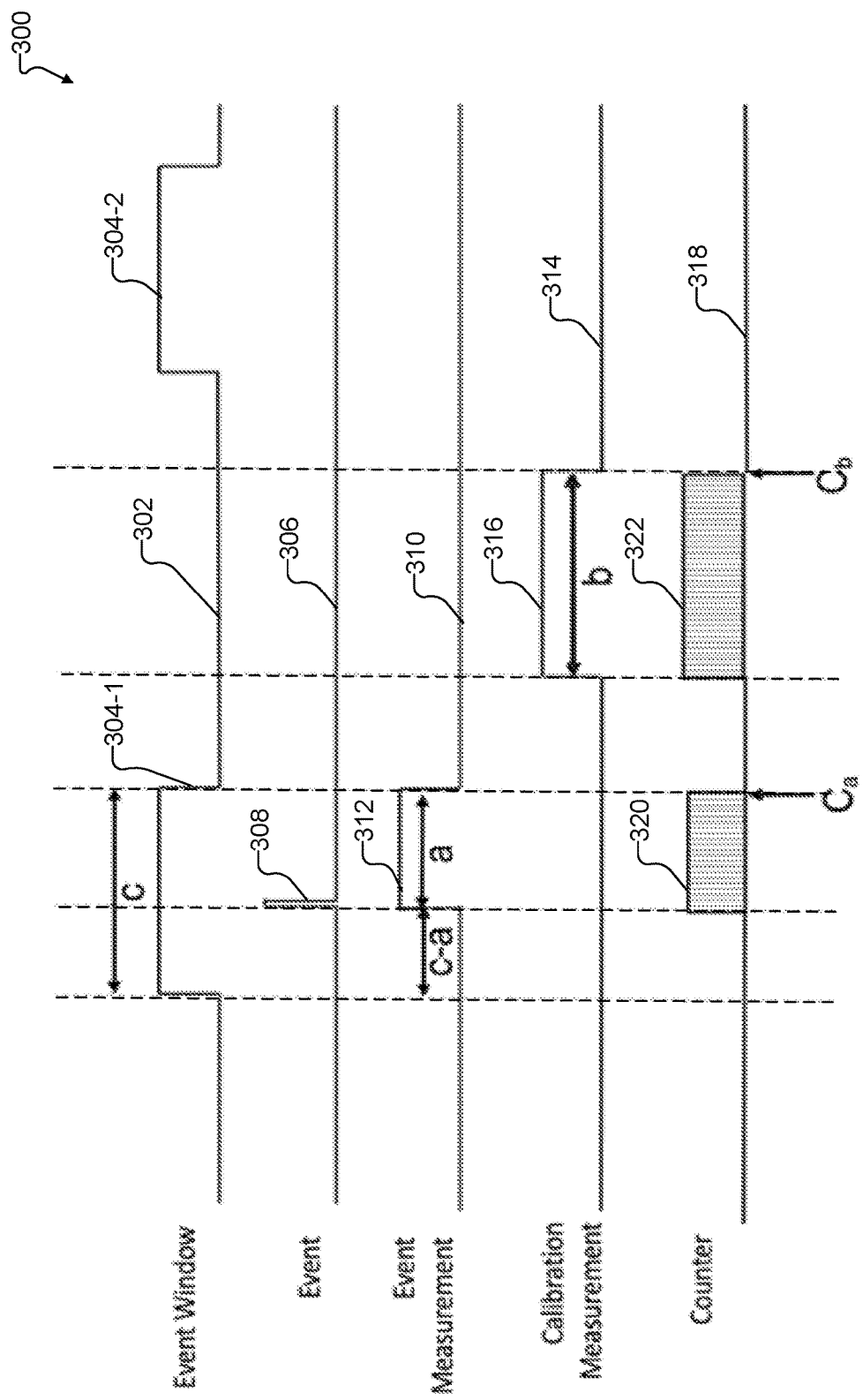
FIG. 3 illustrates an exemplary timing diagram for a photodetector with a low-power TDC architecture according to principles described herein.

SPAD circuit 204 (e.g., an implementation of photodetector 104) may include a SPAD and a fast gating circuit configured to arm and disarm the SPAD. The fast gating circuit may also be configured to output a signal triggered by an event in which the SPAD detects a photon. The signal is configured to enable a GRO of TDC 206 upon receipt of the signal by TDC 206. For example, GRO 208 may be enabled based on receiving the signal from SPAD circuit 204. TDC 206 may use GRO 208 (along with other components such as counter 210 and/or bias generator 212) to determine an arrival time of the photon at the SPAD. For instance, TDC 206 may determine the arrival time of the photon based on an exemplary timing diagram 300 as shown in FIG. 3.

Timing diagram 300 depicts an event window pulse wave 302 showing predetermined event detection time windows 304, such as a first predetermined event detection time window 304-1 (of a length 'c') and a second predetermined event detection time window 304-2. Predetermined event detection time windows 304 may be generated by control circuit 216 in response to a light pulse being applied to a target. Predetermined event detection time windows 304 may correspond to lengths of time the SPAD is armed and enabled to detect a photon of the light pulse. Predetermined event detection time windows 304 may start subsequent to the respective light pulses. As described above, in some examples, predetermined event detection time windows 304 may start after a specified delay after the respective light pulses. In other examples, predetermined event detection time windows 304 may start substantially immediately after the respective light pulses.

An event pulse wave 306 shows an event 308 in which SPAD circuit 204 detects a photon. As shown, event 308 occurs during first predetermined event detection time window 304-1. Event 308 may trigger a signal output by SPAD circuit 204 and received by TDC 206. Based on receiving the signal, GRO 208 may be enabled to measure a time interval between when event 308 occurred and an end of first predetermined event detection time window 304-1. The time interval is shown by an event measurement 312 (of a length 'a') of an event measurement pulse wave 310. Timing diagram 300 further includes a counter pulse wave 318 that shows a value of counter 210 corresponding to measurements determined by GRO 208. For instance, a first count 320 corresponds to event measurement 312 and provides a digital value, $C_a$, proportional to time interval 'a'. Thus, TDC 206 may determine an arrival time of the photon at event 308 based on $C_a$ and known length 'c' of first predetermined event detection time window 304-1, which corresponds to (c−a).

In addition, timing diagram 300 includes a calibration measurement pulse wave 314 that shows a calibration measurement 316 of a length V. Calibration measurement 316 may be measured using GRO 208 to provide a calibration factor for determining the arrival time of the photon at event 308. For example, using GRO 208, TDC 206 may measure a calibration window, which may be generated by control circuit 216. Counter pulse wave 318 shows a second count 322 of counter 210 corresponding to calibration measurement 316. Second count 322 provides a digital value, $C_b$, proportional to time interval V. Using $C_b$, TDC 206 may calibrate GRO 208 and determine the arrival time of the photon at event 308 further based on $C_b$. For example, TDC 206 may determine the arrival time based on an equation such as $$T_{c-a} = T_c \times \left(1 - \frac{C_a}{C_b}\right) \quad \text{(Equation 1)}$$

where $T_{c-a}$ is the arrival time of the photon at event 308 and $T_c$ is a time of first predetermined event detection time window (e.g., event detection time window 304-1). As predetermined event detection time windows and calibration windows may be generated by control circuit 216, lengths of such windows may be of known quantities and may also be set to a same length such that b=c.

Using such an exemplary timing of signals as shown in timing diagram 300, TDC 206 may be implemented as an event-based TDC and/or include event-based components. For example, photodetector system 200 (e.g., control circuit 216, TDC 206) may keep GRO 208 disabled until event 308 occurs (and/or TDC 206 may be disabled with GRO 208), which may conserve power, especially for applications in which events are relatively infrequent. Photodetector system 200 may enable GRO 208 upon receiving a signal from SPAD circuit 204 triggered by event 308 and determine the arrival time of the photon at event 308 using GRO 208. Subsequent to the determining, photodetector system 200 may disable GRO 208 until another event triggered by detection of a photon and/or a calibration measurement. Additionally or alternatively, photodetector system 200 may keep GRO 208 enabled to perform the calibration of GRO 208. Such calibration measurements may be performed at any suitable frequency, such as after each event measurement, after a certain number of event measurements, after a specified amount of time has elapsed since a previous calibration, etc.

In some examples, GRO 208 may be used to determine a fine count for the timing of event 308, while PLL 214 provides a signal to bias generator 212 that provides a course count. PLL 214 may be locked to an external reference clock and provide an analog voltage to bias generator 212. In other examples, photodetector system 200 may be implemented without PLL 214 and/or bias generator 212. In such examples, GRO 208 may be free running, with a starting and stopping determined by a digital enable signal. Examples of GRO 208 are described herein.

Figure 4:
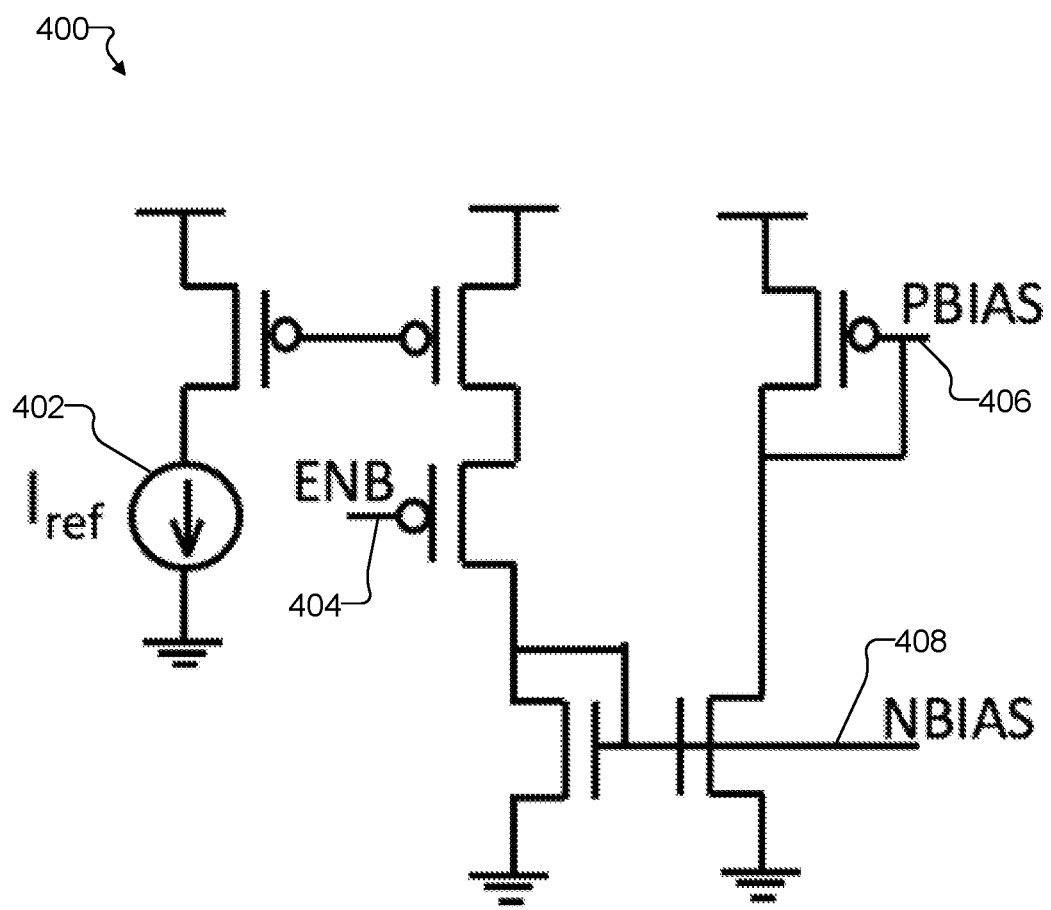
FIGS. 4-8 illustrate exemplary circuits for components for low-power TDC architectures according to principles described herein.

FIG. 4 illustrates an exemplary circuit 400 implementing a bias generator (e.g., bias generator 212). Circuit 400 includes a reference current source 402, such as a reference received from PLL 214. Circuit 400 shows a current mirror gated by an enable signal 404. Enable signal 404 may be an analog signal provided in response to event 308, when SPAD circuit 204 detects a photon. While enable signal 404 is received, circuit 400 may generate an analog bias via a first output PBIAS 406 and a second output NBIAS 408 to be provided to GRO 208. Conversely, while enable signal 404 is stopped, circuit 400 may stop providing the analog bias to GRO 208.

Figure 5:
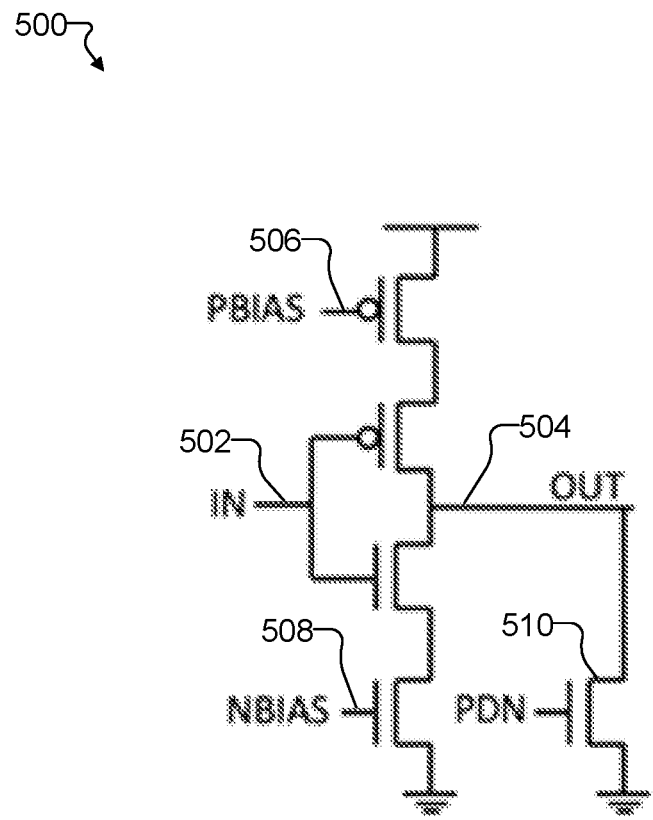

FIG. 5 illustrates an exemplary circuit 500 implementing an inverter of GRO (e.g., GRO 208) configured to operate with a bias generator (e.g., bias generator 212). Circuit 500 shows an inverter configured to receive a signal at an input 502 and generate an inverted signal at an output 504. GRO 208 may include a plurality of inverters coupled such that output 504 of one inverter is connected to an input 502 of a next inverter to form a ring of inverters. Circuit 500 shows a current-starved inverter configured to receive the analog bias from bias generator 212 via a first input PBIAS 506 and a second input NBIAS 508. Circuit 500 also includes a pulldown transistor 510 to implement a tri-state output (e.g., a high impedance state) for the inverter. Further, pulldown transistor 510 may also be configured to initialize a state of circuit 500 so that GRO 208 may start each time in a same initialization state.

While the analog bias is being received, GRO 208 may oscillate, providing a signal to a counter (e.g., counter 210), which may be used to determine a digital representation of a time, such as an arrival time of a photon. Once the analog bias is stopped, GRO 208 may be disabled and the inverters of GRO 208 put into the high impedance state. GRO 208 may further include components configured to store a value of GRO 208, as shown in FIG. 6.

Figure 6:
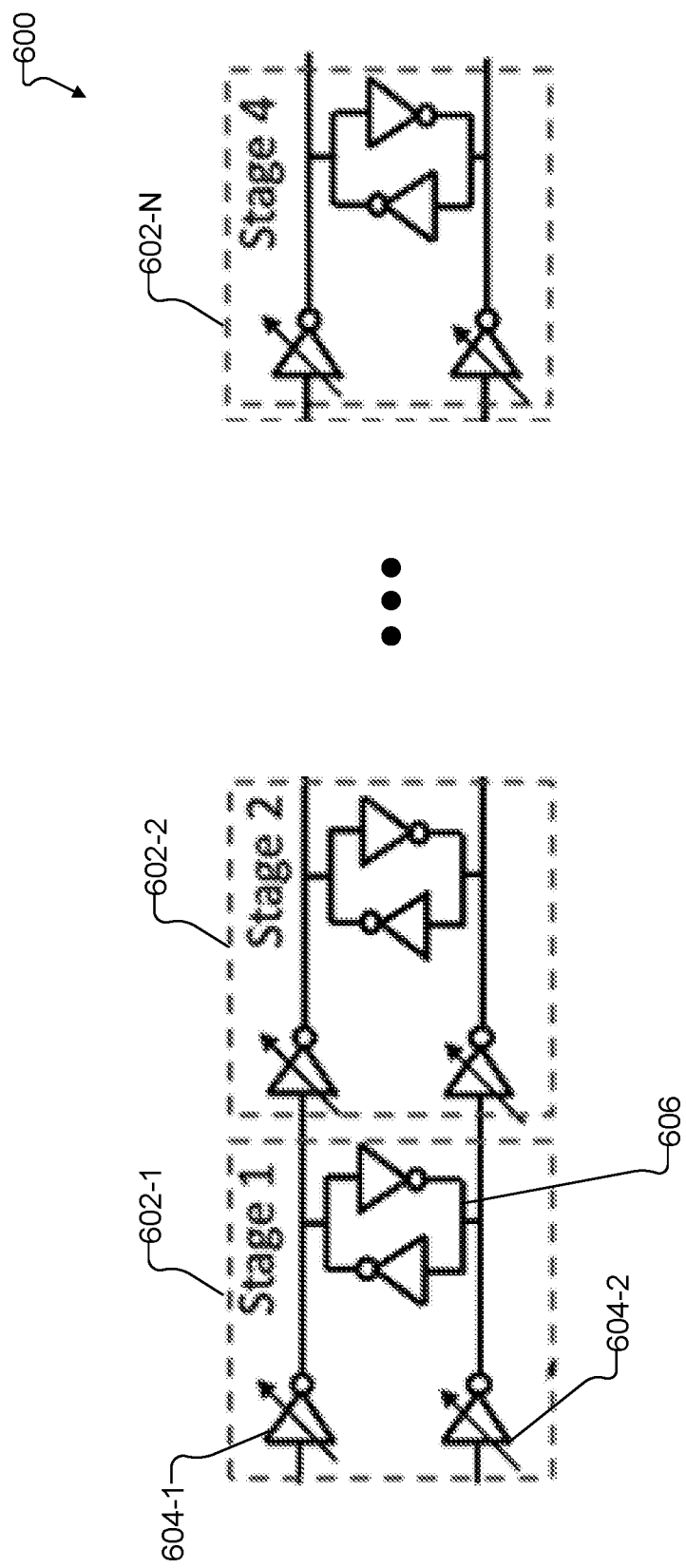

FIG. 6 illustrates an exemplary circuit 600 implementing a GRO (e.g., GRO 208). Circuit 600 shows a plurality of stages 602 (e.g., stage 602-1 through stage 602-N). While stages 602 are shown coupled one to a next, stage 602-N may also be coupled to stage 602-1 to form a ring of stages 602.

Each of stages 602, such as stage 602-1 includes a pair of current-starved inverters 604 (e.g., current starved inverters 604-1 and 604-2). Current-starved inverters 604 may be implemented by circuit 500 of FIG. 5. As described, current-starved inverters 604 may receive a value as an input and provide an inversion of the value as an output (e.g., low to high or high to low). Further, current-starved inverters 604 may be tri-state inverters, configured to output a high impedance state when GRO 208 is disabled. Stage 602-1 further includes a pair of cross-coupled inverters 606 configured to store a value of stage 602-1 when GRO 208 is disabled. In this way, a state of each stage 602 and thus GRO 208 may be internally latched by cross-coupled inverters 606. The latched values may be decoded to determine a fine counter value of TDC 206. By disabling GRO 208 such that GRO 208 stops oscillating, a course counter (e.g., PLL 214) may be gated without any additional circuitry.

Figure 7:
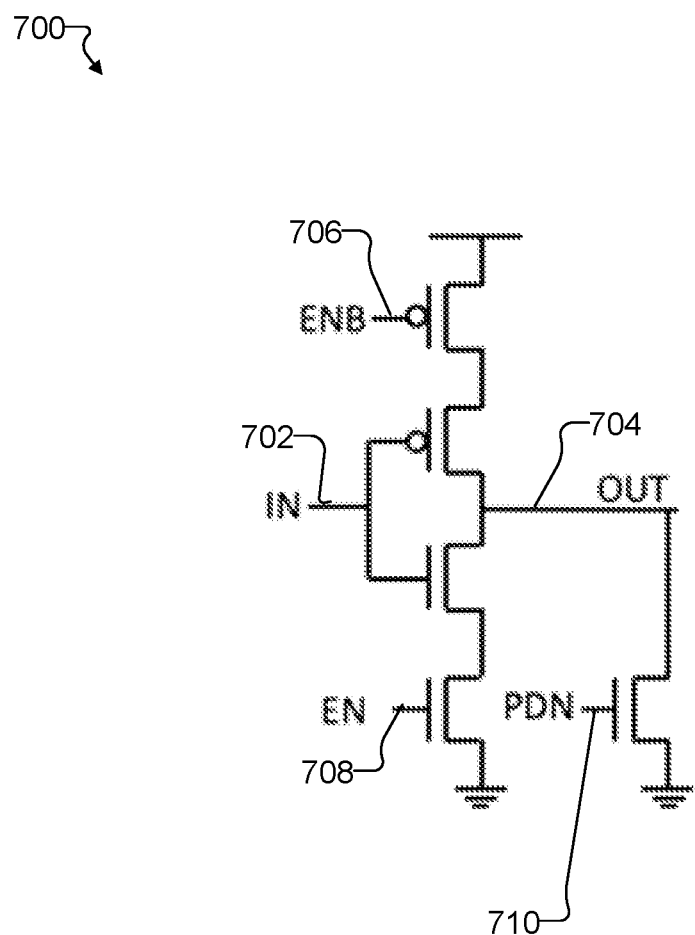

FIG. 7 illustrates an exemplary circuit 700 implementing another inverter of a GRO (e.g., GRO 208). Circuit 700 may also be an implementation of current-starved inverters 604 for circuit 600. Similar to circuit 500, circuit 700 shows an inverter configured to receive a signal at an input 702 and generate an inverted signal at an output 704. The inverter may also be one of a plurality of inverters coupled in a ring to implement GRO 208. However, circuit 700 includes a first input 706 and a second input 708 configured to receive a digital enable signal that turns on and off the inverter and thus GRO 208. Circuit 700 also includes a pulldown transistor 710 to implement a tri-state output (e.g., a high impedance state) for when GRO 208 is disabled.

Circuit 700 may implement GRO 208 to be configured to operate in a free running state, without an external PLL and/or a bias generator. A GRO architecture without such components may allow for reducing layout area and power consumption compared to architectures with such components. However, without a feedback mechanism as provided by the external PLL, process, voltage, and temperature (PVT) variations among inverters of GRO 208 (and across a plurality of GROs) may be significant, affecting measurements provided by GRO 208. But with calibration processes as described herein, effects of such variations may be minimized or offset.

Figure 8:
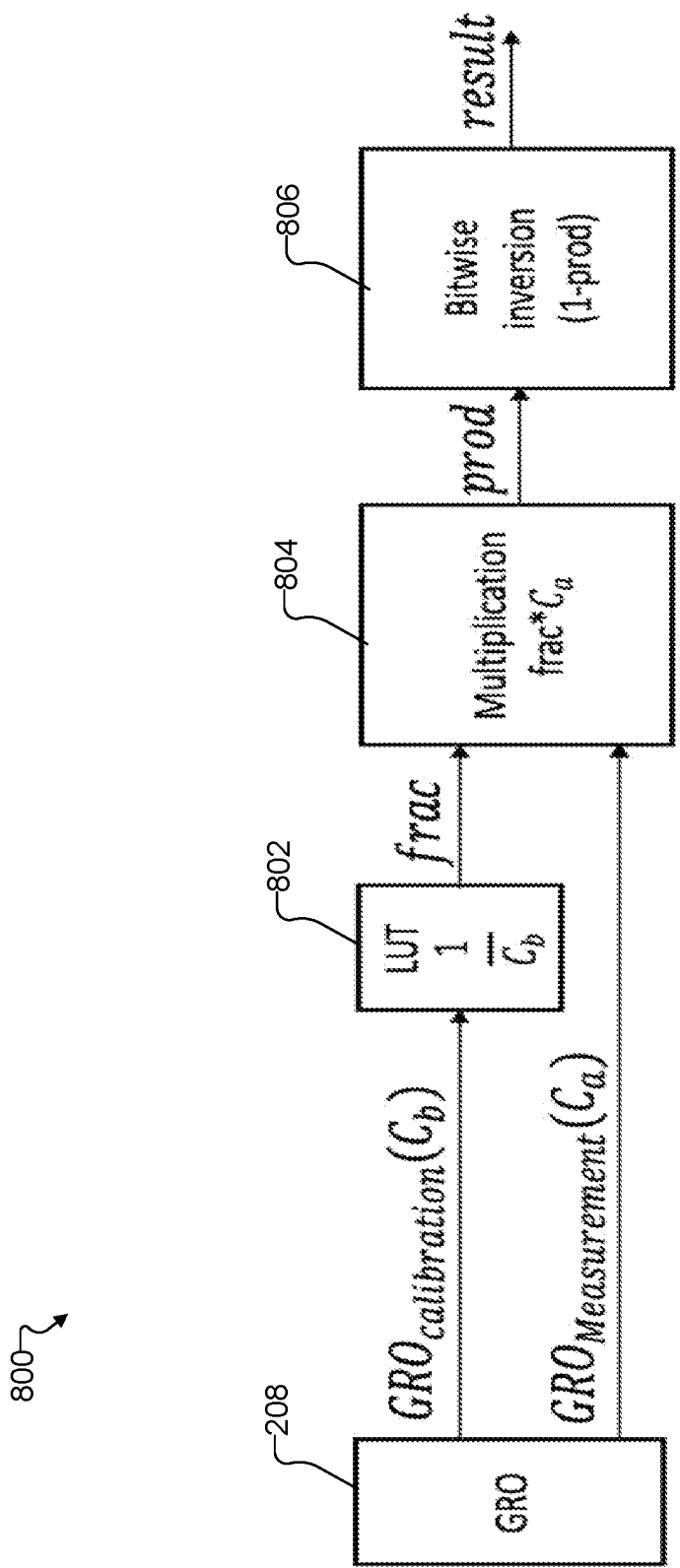

FIG. 8 illustrates an exemplary circuit 800 for a low-power TDC architecture. Circuit 800 shows an implementation for determining an arrival time of an event such as a detection of a photon by a photodetector. Circuit 800 includes GRO 208. GRO 208 provides a measurement output corresponding to an event measurement ($C_a$) and a calibration output corresponding to a calibration measurement ($C_b$). The calibration measurement is received by a lookup table (LUT) component 802. LUT component 802 receives a value for $C_b$, looks up a value corresponding to $1/C_b$, and provides $1/C_b$ as an output to a multiplication component 804. Multiplication component 804 receives $1/C_b$ from LUT component 802 and $C_a$ from GRO 208 and multiplies the two inputs. A product corresponding to $C_a/C_b$ is provided to a bitwise inversion component 806, which calculates one minus $C_a/C_b$ and provides a final result. The final result corresponds to the time of the event, as defined by Equation 1 above.

While circuit 800 shows one example implementation to calculate Equation 1, any suitable combination of components may be used to determine a same result. For example, each and/or all of the calculations described herein may be performed using a lookup table. Alternatively or additionally, the calculation may be performed without a lookup table, using a component configured to perform division along with a component configured to perform multiplication and a component configured to perform subtraction. Further, processing of inputs may be performed to reduce computational complexity, such as using a PLL for course locking to reduce effects of PVT variability and reduce a potential range of calibration and event measurements. Additionally or alternatively, initial trimming may be performed on each GRO 208 to set an operating frequency of GRO 208, reducing variation among GROs. Additionally or alternatively, LUT component 802 may be implemented using a read only memory (ROM) to reduce power and area.

FIG. 9A illustrates an exemplary photodetector system 900 with a low-power TDC architecture. Photodetector system 900 includes a pixel array 902, which includes pixel sub-arrays 904 (e.g., pixel sub-arrays 904-1 and 904-2). Pixel sub-arrays 904 output signals corresponding to events (e.g., detection of a photon by a pixel in a sub-array) and event windows (e.g., predetermined event detection time windows) to a plurality of GROs 906. For example, pixel sub-array 904-1 may output signals corresponding to a first event and a first event window to a first GRO (and/or a first subset of GROs) of the plurality of GROs 906. Pixel sub-array 904-2 may output signals corresponding to a second event and a second event window to a second GRO (and/or a second subset of GROs) of the plurality of GROs 906. However, there may be layout delays depending on a distance between a sub-array and a corresponding GRO in photodetector system 900. Such layout delays may result in incorrect determinations of timing of events. By outputting the signals corresponding to event windows along with the signals corresponding to events, photodetector system 900 may be configured to correct for layout delays.

For example, FIG. 9B shows a timing diagram 920 for photodetector system 900 that shows correction for layout delays. In this example, the first event and the second event may arrive at times relatively close to one another, such that the two times should be grouped into a same time bin. However, due to layout delays, the second event may be received by GROs 906 earlier than the first event, as shown by second event pulse wave 924 and first event pulse wave 928. By providing the signals for the corresponding event windows, photodetector system 900 may determine timing of the events relative to the event windows to compensate for layout delays. As shown in timing diagram 920, second event window pulse wave 922 shows second event window arriving earlier than first event window in first event window pulse wave 926. By taking a difference between arrival times of the event windows or by determining timing of events relative to event windows, such layout delays may be corrected for.

Further, as photodetector systems described herein include a TDC for each SPAD circuit or subset of SPAD circuits, functional testing processes may be improved for such photodetector systems. The plurality of TDCs may allow some or all of the SPAD circuits may be tested simultaneously and/or in parallel, allowing the photodetector systems to test for dark count rate during system startup and/or high-volume manufacturing yield testing.

Figure 10A:
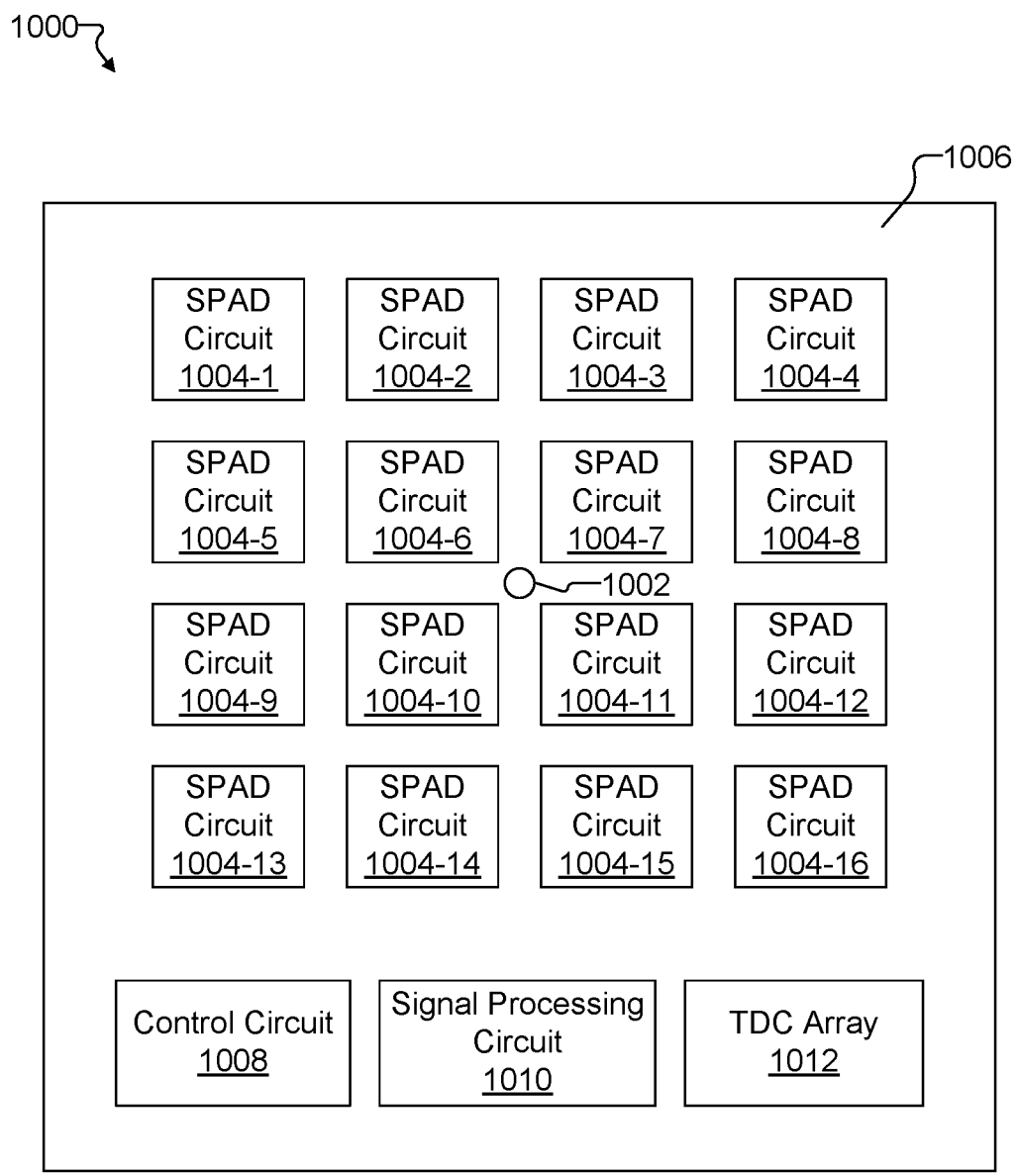
FIG. 10A illustrates an exemplary photodetector system with a low-power TDC architecture according to principles described herein.

FIG. 10A illustrates an exemplary photodetector system 1000 that may be used in accordance with the systems and methods described herein. Photodetector system 1000 may implement any of the photodetector systems described herein. As shown, photodetector system 1000 includes a light source 1002 and a plurality of SPAD circuits 1004 (i.e., SPAD circuits 1004-1 through 1004-16) disposed on a printed circuit board (PCB) 1006. Alternatively, SPAD circuits 1004 (and the other components of photodetector system 1000) may be disposed on an ASIC. Photodetector system 1000 further includes a control circuit 1008 common to SPADs 1004, a signal processing circuit 1010 common to SPADs 1004, and a TDC array 1012 that includes a plurality of TDCs (as described herein) each corresponding to one of the SPAD circuits 1004. Control circuit 1008, signal processing circuit 1010, and TDC array 1012 may each be disposed on PCB 1006, as shown in FIG. 10A, or located elsewhere within photodetector system 1000. Each SPAD circuit 1004 in combination with a TDC included in TDC array 1012, control circuit 1008, and signal processing circuit 1004 may implement a particular photodetector. Hence, photodetector system 1000 may be said to include an array of photodetectors.

Light source 1002 may be configured to generate one or more light pulses at one or more wavelengths that may be applied to a desired target (e.g., a target within the brain). Light source 1002 may be implemented by any suitable combination of components. For example, light source 1002 may be implemented by a laser source that generates laser pulses. Light source may be implemented on PCB 1006 or external to PCB 1006.

SPAD circuits 1004 may be configured to detect photons of a light pulse generated by light source 1002 after the photons reflect or scatter from a target (e.g., a target internal to a user, such as brain tissue). SPAD circuits 1004 may also be used to detect photons reflected from any object due to ambient light for imaging applications. In this case, light source 1002 is not needed since the photons are generated by either ambient light or another light source.

As shown, SPAD circuits 1004 are arranged in a four-by-four array on PCB 1006. The positioning of each SPAD circuit 1004 may correspond, for example, to a pixel within a pixel array. SPAD circuits 1004 may alternatively be arranged in any suitable manner. While sixteen SPAD circuits 1004 are shown in FIG. 10A, it will be recognized that any number of SPAD circuits 1004 may be included in photodetector system 1000.

Control circuit 1008 may be similar in function to control circuit 106, and may be configured to control each of SPAD circuits 1008. Signal processing circuit 1010 may be similar in function to signal processing circuit 110, and may be configured to process signals output by each of SPAD circuits 1004. TDC array 1012 may include a plurality of TDCs each similar to TDC 108 and configured to measure a time difference between the occurrence of a light pulse 1002 and output pulses generated by each of SPAD circuits 1004.

Photodetector system 1000 may be implemented by or included in any suitable device. For example, photodetector system 1000 may be included in a non-invasive wearable device that a user may wear to perform one or more diagnostic, imaging, and/or consumer-related operations.

Figure 10B:
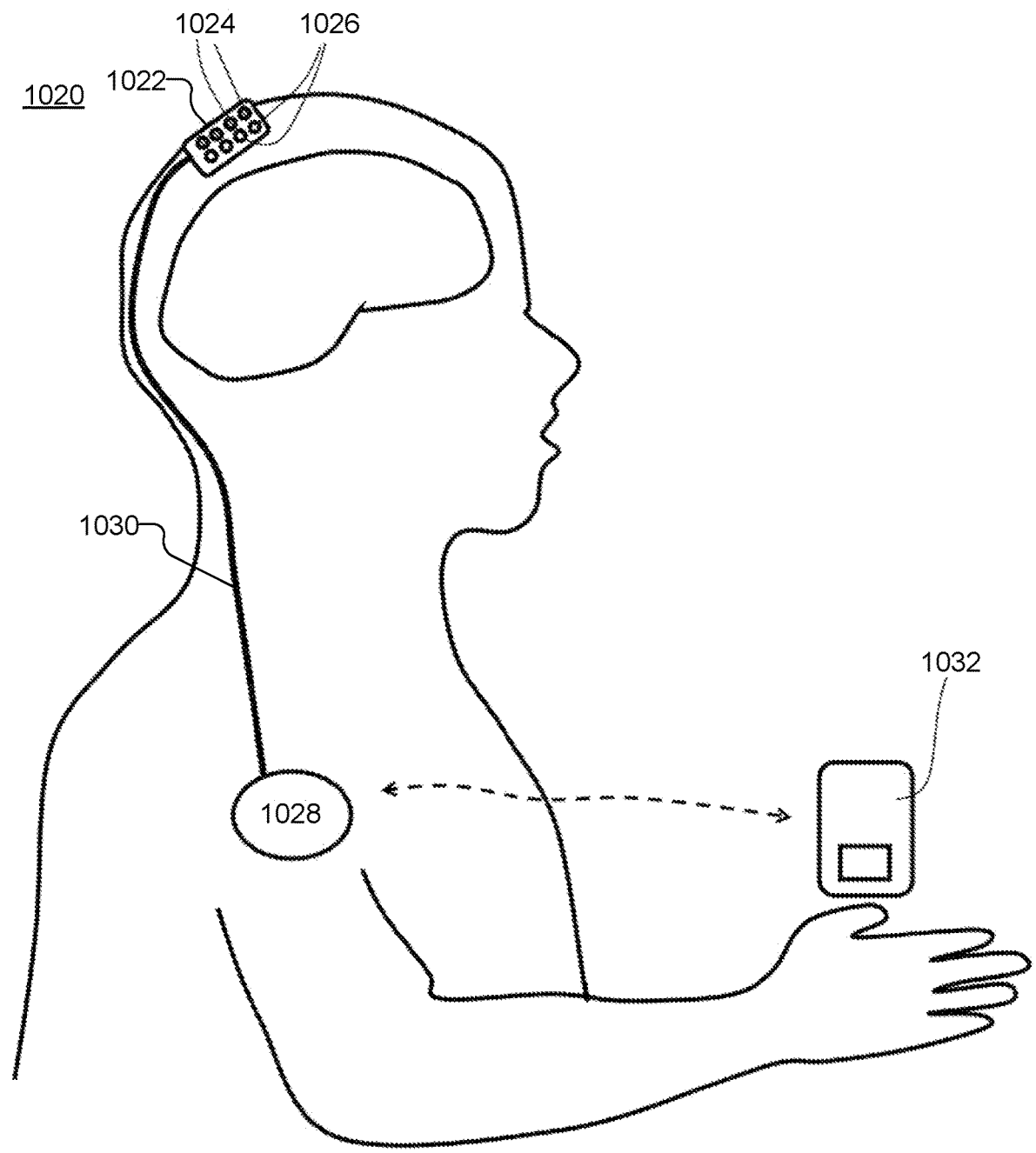
FIG. 10B illustrates an exemplary wearable device including a photodetector system with a low-power TDC architecture according to principles described herein.

To illustrate, FIG. 10B shows an exemplary non-invasive wearable brain interface system 1020 ("brain interface system 1020") that implements a photodetector system, which may be similar to photodetector system 1000. As shown, brain interface system 1020 includes a head-mountable component 1022 configured to be attached to a user's head. Head-mountable component 1022 may be implemented by a cap shape that is worn on a head of a user. Alternative implementations of head-mountable component 1022 include helmets, beanies, headbands, other hat shapes, or other forms conformable to be worn on a user's head, etc. Head-mountable component 1022 may be made out of any suitable cloth, soft polymer, plastic, hard shell, and/or any other suitable material as may serve a particular implementation. Examples of headgears used with wearable brain interface systems are described more fully in U.S. Pat. No. 10,340,408, incorporated herein by reference in its entirety.

Head-mountable component 1022 includes a plurality of photodetectors 1024 and a plurality of light sources 1026 configured to generate light pulses. It will be recognized that in some alternative embodiments, head-mountable component 1022 may include a single photodetector 1024 and/or a single light source 1026. For example, brain interface system 1020 may be used for controlling an optical path and for transforming photodetector pixel measurements into an intensity value that represents an optical property of a brain tissue region. Brain interface system 1020 allows optical detection of deep anatomical location through skin and bone by extracting data from photons originating from light source 1026 to a target location within the user's brain, in contrast to traditional imaging systems and methods (e.g., optical coherence tomography (OCT)), which only image superficial tissue structures or through optically transparent structures.

Brain interface system 1020 may further include a processor 1028 configured to communicate with (e.g., control and/or receive signals from) photodetectors 1024 and light sources 1026 by way of a communication link 1030. Communication link 1030 may include any suitable wired and/or wireless communication link. Processor 1028 may include any suitable housing and may be located on the user's scalp, neck, shoulders, chest, or arm, as may be desirable. In some variations, processor 1028 may be integrated in the same assembly housing as photodetectors 1024 and light sources 1026.

As shown, brain interface system 1020 may optionally include a remote processor 1032 in communication with processor 1028. For example, remote processor 1032 may store measured data from photodetectors 1024 and/or processor 1028 from previous detection sessions and/or from multiple brain interface systems (not shown). Power for photodetectors 1024, light sources 1026, and/or processor 1028 may be provided via a wearable battery (not shown). In some examples, processor 1028 and the battery may be enclosed in a single housing, and wires carrying power signals from processor 1028 and the battery may extend to photodetectors 1024 and light sources 1026. Alternatively, power may be provided wirelessly (e.g., by induction).

In some alternative embodiments, head-mountable component 1022 does not include individual light sources. Instead, a light source configured to generate the light that is detected by photodetector 1024 may be included elsewhere in brain interface system 1020. For example, a light source may be included in processor 1028 and coupled to photodetector units 1024 through electrical connections.

Each of the light sources described herein may be implemented by any suitable device. For example, a light source as used herein may be, for example, a distributed feedback (DFB) laser, a super luminescent diode (SLD), a light emitting diode (LED), a diode-pumped solid-state (DPSS) laser, a laser diode (LD), a super luminescent light emitting diode (sLED), a vertical-cavity surface-emitting laser (VCSEL), a titanium sapphire laser, a micro light emitting diode (mLED), and/or any other suitable laser or light source.

Photodetector system 1000 shown in FIG. 10A may alternatively be included in a non-wearable device (e.g., a medical device and/or consumer device that is placed near the head or other body part of a user to perform one or more diagnostic, imaging, and/or consumer-related operations). Photodetector system 1000 may alternatively be included in a sub-assembly enclosure of a wearable invasive device (e.g., an implantable medical device for brain recording and imaging).

Any suitable SPAD circuits may be used in the photodetector architectures described herein. Some of the SPAD circuits described herein are gated with a capacitor (or, in some cases, with a parasitic capacitance of the SPAD itself) that is pre-charged with a bias voltage before a command is provided to arm the SPAD. This is described more fully in U.S. Pat. No. 10,158,038, incorporated above by reference in its entirety.

Figure 11:
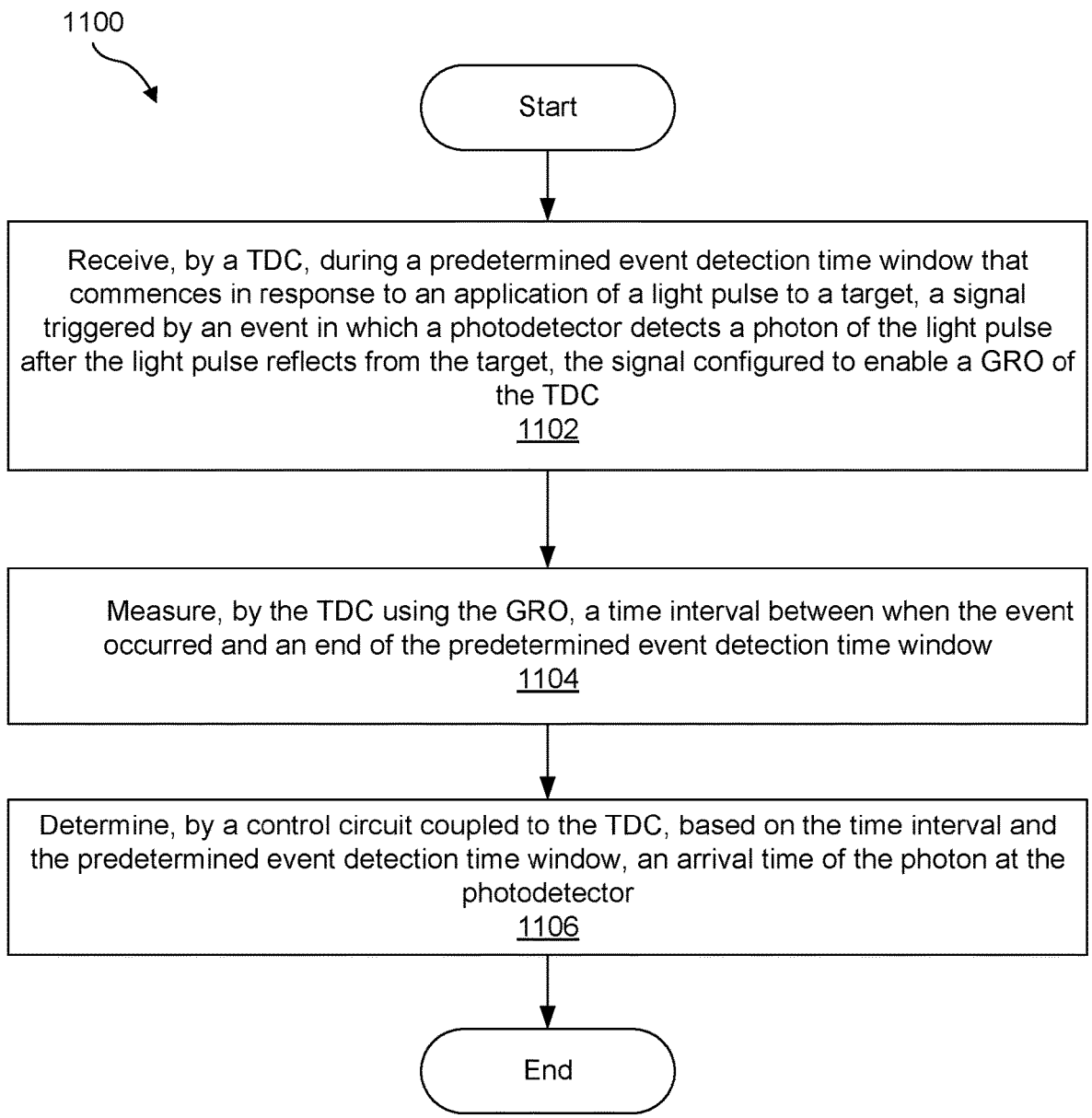
FIG. 11 illustrates an exemplary method according to principles described herein.

FIG. 11 illustrates an exemplary method 1100 for measuring time intervals using a photodetector system with a low-power TDC architecture (e.g., any of the photodetector systems described herein). While FIG. 11 illustrates exemplary operations according to one embodiment, other embodiments may omit, add to, reorder, and/or modify any of the operations shown in FIG. 11.

In operation 1102, a TDC receives, during a predetermined event detection time window that commences in response to an application of a light pulse to a target, a signal triggered by an event in which the photodetector detects a photon of the light pulse after the light pulse reflects from the target, the signal configured to enable a GRO of the TDC. Operation 1102 may be performed in any of the ways described herein.

In operation 1104, the TDC measures, using the GRO, a time interval between when the event occurred and an end of the predetermined event detection time window. Operation 1104 may be performed in any of the ways described herein.

In operation 1106, a control circuit coupled to the TDC determines, based on the time interval and the predetermined event detection time window, an arrival time of the photon at the photodetector. Operation 1106 may be performed in any of the ways described herein.

Figure 12:
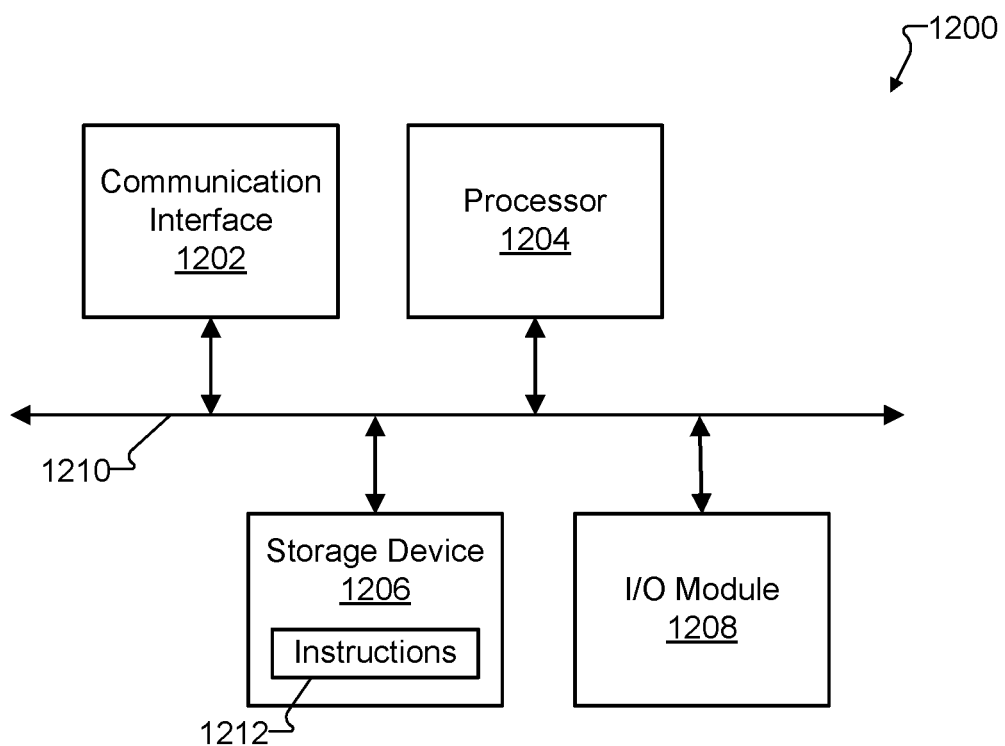
FIG. 12 illustrates an exemplary computing device according to principles described herein.

FIG. 12 illustrates an exemplary computing device 1200 that may be specifically configured to perform one or more of the processes described herein. As shown in FIG. 12, computing device 1200 may include a communication interface 1202, a processor 1204, a storage device 1206, and an input/output ("I/O") module 1208 communicatively connected one to another via a communication infrastructure 1210. While an exemplary computing device 1200 is shown in FIG. 12, the components illustrated in FIG. 12 are not intended to be limiting. Additional or alternative components may be used in other embodiments. Components of computing device 1200 shown in FIG. 12 will now be described in additional detail.

Communication interface 1202 may be configured to communicate with one or more computing devices. Examples of communication interface 1202 include, without limitation, a wired network interface (such as a network interface card), a wireless network interface (such as a wireless network interface card), a modem, an audio/video connection, and any other suitable interface.

Processor 1204 generally represents any type or form of processing unit capable of processing data and/or interpreting, executing, and/or directing execution of one or more of the instructions, processes, and/or operations described herein. Processor 1204 may perform operations by executing computer-executable instructions 1212 (e.g., an application, software, code, and/or other executable data instance) stored in storage device 1206.

Storage device 1206 may include one or more data storage media, devices, or configurations and may employ any type, form, and combination of data storage media and/or device. For example, storage device 1206 may include, but is not limited to, any combination of the non-volatile media and/or volatile media described herein. Electronic data, including data described herein, may be temporarily and/or permanently stored in storage device 1206. For example, data representative of computer-executable instructions 1212 configured to direct processor 1204 to perform any of the operations described herein may be stored within storage device 1206. In some examples, data may be arranged in one or more databases residing within storage device 1206.

I/O module 1208 may include one or more I/O modules configured to receive user input and provide user output. I/O module 1208 may include any hardware, firmware, software, or combination thereof supportive of input and output capabilities. For example, I/O module 1208 may include hardware and/or software for capturing user input, including, but not limited to, a keyboard or keypad, a touchscreen component (e.g., touchscreen display), a receiver (e.g., an RF or infrared receiver), motion sensors, and/or one or more input buttons.

I/O module 1208 may include one or more devices for presenting output to a user, including, but not limited to, a graphics engine, a display (e.g., a display screen), one or more output drivers (e.g., display drivers), one or more audio speakers, and one or more audio drivers. In certain embodiments, I/O module 1208 is configured to provide graphical data to a display for presentation to a user. The graphical data may be representative of one or more graphical user interfaces and/or any other graphical content as may serve a particular implementation.

In some examples, any of the systems, computing devices, processors, controller units, and/or other components described herein may be implemented by computing device 1200. For example, control circuit 106, signal processing circuit 110 and/or control circuit 216 may be implemented by processor 1204.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A system comprising:
   a component configured to be worn on a body of a user, the component comprising a time-to-digital converter (TDC) configured to:
   receive, during a predetermined event detection time window that commences in response to an application of a light pulse to a target within the body, a signal triggered by an event in which a photodetector detects a photon of the light pulse after the light pulse reflects from the target; and
   measure, based on the receiving the signal, a time interval between when the event occurred and an end of the predetermined event detection time window; and
   a processor configured to determine, based on the time interval and the predetermined event detection time window, an arrival time of the photon at the photodetector.

2. The system of claim 1, wherein:
   the signal is configured to enable a gated ring oscillator (GRO) of the TDC; and
   the measuring is performed using the GRO.

3. The system of claim 2, wherein the signal is further configured to:
   enable the GRO of the TDC while the signal is being received by the TDC; and
   disable the GRO of the TDC upon a stopping of the signal.

4. The system of claim 2, wherein the TDC is further configured to receive, subsequent to the predetermined event detection time window, a second signal configured to disable the GRO of the TDC.

5. The system of claim 4, wherein the second signal is received upon completion of the predetermined event detection time window.

6. The system of claim 2, wherein:
   the GRO includes one or more pairs of cross-coupled inverters configured to store a state of the GRO when the GRO is disabled; and
   the measuring the time interval includes decoding the stored state of the GRO.

7. The system of claim 6, wherein:
   the TDC receives a voltage from a phase-locked loop (PLL) or a delay-locked loop (DLL) that provides an external reference clock; and
   at least one of the enabling the GRO and the measuring the time interval is based additionally on the received voltage.

8. The system of claim 1, wherein:
   the TDC is further configured to measure an additional time interval subsequent to the time interval;
   the processor is further configured to calibrate the TDC based on the measured additional time interval; and
   the determining the arrival time of the photon is further based on the calibrating.

9. The system of claim 8, wherein the additional time interval is a same or substantially similar length as the predetermined event detection time window.

10. The system of claim 8, further comprising a calibration circuit configured to provide calculations for the calibrating the TDC.

11. The system of claim 8, further comprising a lookup table configured to provide calculations for the calibrating the TDC.

12. The system of claim 1, wherein:
the TDC is further configured to receive an event window signal specifying a starting time of the predetermined event detection time window; and
the determining the arrival time of the photon is further based on the starting time of the predetermined event detection time window.

13. The system of claim 1, wherein the photodetector comprises:
a single photon avalanche diode (SPAD); and
a fast gating circuit configured to arm and disarm the SPAD.

14. The system of claim 1, wherein the component is implemented by a non-invasive wearable brain interface system.

15. The system of claim 1, further comprising a wearable battery configured to provide power to the component.

16. A system comprising:
a time-to-digital converter (TDC) configured to:
receive, during a predetermined event detection time window that commences in response to an application of a light pulse to a target, a signal triggered by an event in which a photodetector detects a photon of the light pulse after the light pulse reflects from the target; and
measure, based on the receiving the signal, a time interval between when the event occurred and an end of the predetermined event detection time window; and
a processor configured to determine, based on the time interval and the predetermined event detection time window, an arrival time of the photon at the photodetector.

17. The system of claim 1, wherein:
the signal is configured to enable a gated ring oscillator (GRO) of the TDC; and
the measuring is performed using the GRO.

18. The system of claim 17, wherein the signal is further configured to:
enable the GRO of the TDC while the signal is being received by the TDC; and
disable the GRO of the TDC upon a stopping of the signal.

19. The system of claim 17, wherein the TDC is further configured to receive, subsequent to the predetermined event detection time window, a second signal configured to disable the GRO of the TDC.

20. A method comprising:
receiving, by a time-to-digital converter (TDC), during a predetermined event detection time window that commences in response to an application of a light pulse to a target, a signal triggered by an event in which a photodetector detects a photon of the light pulse after the light pulse reflects from the target;
measuring, by the TDC based on the receiving the signal, a time interval between when the event occurred and an end of the predetermined event detection time window; and
determining, based on the time interval and the predetermined event detection time window, an arrival time of the photon at the photodetector.

* * * * *